(12) United States Patent
Orwig et al.

(10) Patent No.: US 12,280,075 B2
(45) Date of Patent: Apr. 22, 2025

(54) ULTRASOUND-GUIDED RETE TESTIS INJECTION/ASPIRATION DEVICE

(71) Applicant: University of Pittsburgh—Of the Commonwealth System of Higher Education, Pittsburgh, PA (US)

(72) Inventors: Kyle E. Orwig, Wexford, PA (US); Hanna Valli-Pulaski, Coraopolis, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1028 days.

(21) Appl. No.: 17/272,713

(22) PCT Filed: Dec. 6, 2019

(86) PCT No.: PCT/US2019/065006
§ 371 (c)(1),
(2) Date: Mar. 2, 2021

(87) PCT Pub. No.: WO2020/118214
PCT Pub. Date: Jun. 11, 2020

(65) Prior Publication Data
US 2021/0369783 A1 Dec. 2, 2021

Related U.S. Application Data

(60) Provisional application No. 62/776,690, filed on Dec. 7, 2018.

(51) Int. Cl.
*A61M 5/142* (2006.01)
*A61K 9/00* (2006.01)
(Continued)

(52) U.S. Cl.
CPC ............ *A61K 35/28* (2013.01); *A61K 9/0019* (2013.01); *A61M 5/1422* (2013.01);
(Continued)

(58) Field of Classification Search
CPC .. A61B 2017/3413; A61M 2005/1403; A61M 2210/161; A61M 5/1582; A61M 5/16827; A61M 5/172; A61P 15/00
See application file for complete search history.

(56) References Cited

U.S. PATENT DOCUMENTS 4,269,174 A * 5/1981 Adair .................. A61F 6/22
606/49
4,576,161 A * 3/1986 Mikkelson ......... A61B 17/3403
128/843
(Continued)

FOREIGN PATENT DOCUMENTS

EP 1967147 9/2008
EP 2468351 6/2012

OTHER PUBLICATIONS

English translation of EP1967147A2 (Year: 2008).*
(Continued)

*Primary Examiner* — Christine H Matthews
(74) *Attorney, Agent, or Firm* — Klarquist Sparkman, LLP

(57) ABSTRACT

Ultrasound-guided rete testis injection/aspiration devices and methods are described. Some methods include inserting a needle into the rete testis space of a patient and injecting a therapeutic medium through the needle into the rete testis space and seminiferous tubules of the testis. The therapeutic medium can help to treat infertility. In some examples, the method can include monitoring intra-testicular pressure of the patient. In some examples, the therapeutic medium can include stem cells. In some examples, the therapeutic medium can include gene therapy vectors. In some
(Continued)

examples, the method can include flushing the rete testis space and seminiferous tubules with a saline solution through the needle. Exemplary devices can include a dual lumen needle, a collection tube, a dual function pump, and flexible tubing. The dual function pump can include a dual syringe pump and a vacuum pump.

20 Claims, 2 Drawing Sheets

(51) Int. Cl.
    *A61K 35/28*     (2015.01)
    *A61M 5/158*     (2006.01)
    *A61M 5/42*     (2006.01)
    *A61K 48/00*     (2006.01)

(52) U.S. Cl.
    CPC .......... *A61M 5/1582* (2013.01); *A61M 5/427* (2013.01); *A61K 48/00* (2013.01); *A61M 2205/3344* (2013.01); *A61M 2210/161* (2013.01)

(56) References Cited

U.S. PATENT DOCUMENTS

| | | | |
|---|---|---|---|
| 4,920,982 A * | 5/1990 | Goldstein | A61B 18/1477 606/49 |
| 5,858,354 A | 1/1999 | Brinster | |
| 6,215,039 B1 | 4/2001 | Brinster | |
| 2004/0225180 A1 | 11/2004 | Junger | |
| 2015/0374929 A1 * | 12/2015 | Hyde | A61M 5/3286 604/239 |

OTHER PUBLICATIONS

Hermann et al., "Spermatogonial Stem Cell Transplantation into Rhesus Testes Regenerates Spermatogenesis Producing Functional Sperm," *Cell Stem Cell*, 11:715-726 (Nov. 2, 2012).

International Search Report and Written Opinion for related International Application No. PCT/US2019/065006, 12 pages, mailed Mar. 22, 2020.

Kojima et al., "Therapeutic Potential of Gene Transfer to Testis; Myth or Reality?" *Gene Therapy Applications*, pp. 279-296 (Aug. 23, 2011).

Orwig, "Retrieval of Sperm From Men with Azoospermia Using ultrasound-guided Rete Testis Aspiration" https://clinicaltrials.gov/ct2/history/NCT03291522?V_2=View#StudyPageTop, 7 pages, downloaded Feb. 26, 2021.

Schlatt et al., "Germ cell transfer into rat, bovine, monkey and human testes," *Human Reproduction*, 14(1): 144-150 (Jan. 1999).

* cited by examiner

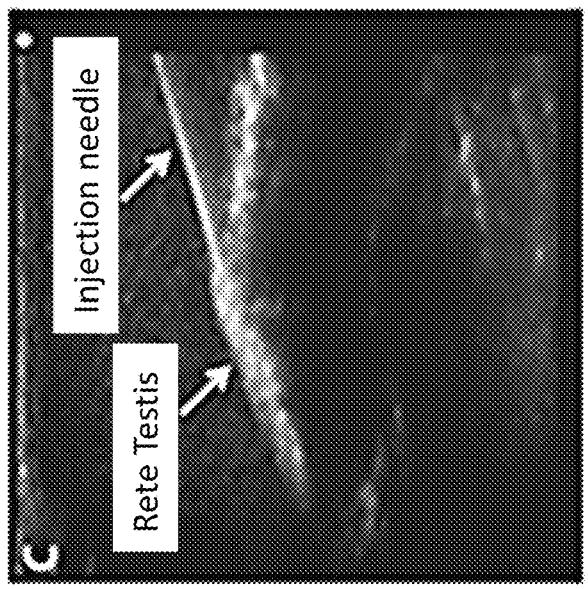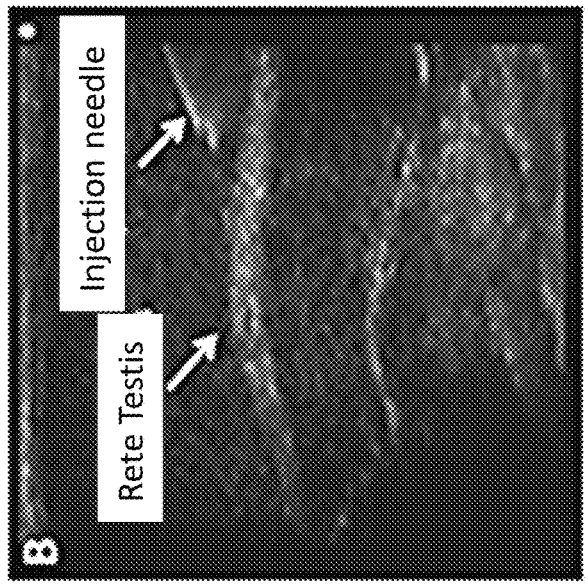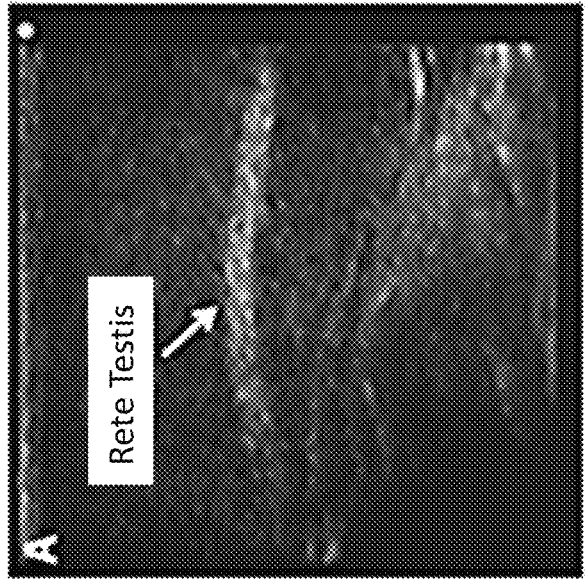

ULTRASOUND-GUIDED RETE TESTIS INJECTION/ASPIRATION DEVICE

CROSS-REFERENCE TO RELATED APPLICATIONS

This application is the U.S. National Stage of International Application No. PCT/US2019/065006, filed Dec. 6, 2019, which claims the benefit of U.S. Provisional Patent Application No. 62/776,690 filed Dec. 7, 2018, which is incorporated by reference herein in its entirety.

ACKNOWLEDGMENT OF GOVERNMENT SUPPORT

This disclosure was made with Government support under grant #HD055475 awarded by the National Institute of Health. The government has certain rights in the invention.

FIELD

The present disclosure relates to ultrasound-guided rete testis injection/aspiration devices and to methods related to such devices.

BACKGROUND

In the United States, it is estimated that 10-15% of all men are infertile and 1% of all men in the general population have azoospermia (no sperm in the ejaculated semen), which corresponds to 645,000 men between the ages of 20 and 50 in the USA. For these men, improved fertility treatments are desired.

SUMMARY

Embodiments of an ultrasound-guided rete testis injection/aspiration device are disclosed herein, as well as related methods of use.

Exemplary methods can comprise inserting a needle into the rete testis space of a patient and injecting a therapeutic medium through the needle into the rete testis space and seminiferous tubules of the testis. The therapeutic medium can help to treat infertility.

In some examples, the method can further comprise monitoring intra-testicular pressure of the patient. In some examples, the therapeutic medium can comprise stem cells. In some examples, the therapeutic medium can comprise gene therapy vectors. In some examples, the method can further comprise flushing the rete testis space and seminiferous tubules with a saline solution through the needle.

Exemplary methods can comprise inserting a dual lumen needle into the rete testis space and seminiferous tubules of a patient, wherein the dual lumen needle comprises an outer needle and a recessed inner needle, flushing the rete testis and seminiferous tubules with a saline solution through the outer needle of the dual lumen needle, and aspirating the saline solution with sperm from the rete testis through the inner needle of the dual lumen needle.

In some examples, the method can further comprise monitoring the intra-testicular pressure of the patient to avoid ischemic damage to the testis. In some examples, the method can further comprise collecting the aspirated sperm in a collection tube.

Exemplary apparatus can comprise a dual lumen needle, a collection tube, a dual function pump, and a first, second, and third flexible tube. The dual lumen needle can comprise an outer needle having a first gauge and an inner needle having a second gauge. The first gauge can be larger than the second gauge and the inner needle can be recessed within the outer needle. The dual function pump can comprise a dual syringe pump and a vacuum pump. The dual syringe pump can comprise a first syringe, a second syringe, a pressure sensor, and an injection port. The first syringe and the second syringe can be configured to output the fluid media through the injection port. The vacuum pump can comprise a pump mechanism, a vacuum pressure gauge and an aspiration port. The first flexible tube can connect the injection port to the outer needle of the dual lumen needle. The second flexible tube can connect the aspiration port to the collection tube. The third flexible tube can connect the inner needle of the dual lumen needle to the collection tube.

In some examples, the first, second, and third flexible tubes can comprise polyethylene. In some examples, the inner needle can be configured to aspirate fluid from the testis into the collection tube. In some examples, the outer needle can be configured to inject fluid from the first syringe or the second syringe. In some examples, the dual function pump can be configured to inject a first fluid or fluids through the injection port into the testis and then to aspirate the first fluid or fluids with testicular exudates through the inner needle of the dual lumen needle.

In some examples, the pressure sensor can be configured to monitor intra-testicular pressure of a patient when the dual lumen needle is inserted into the rete testis space of the patient. In some examples, the pump mechanism can be configured to apply vacuum pressure to the aspiration port to cause fluid to be aspirated through the inner needle. In some examples, the vacuum pressure gauge can be configured to monitor vacuum pressure applied to the aspiration port.

In some examples, the outer needle can have a gauge in a range of 23-25 G. In some examples, the inner needle can have a gauge in a range of 28-31 G. In some examples, the apparatus can comprise at least one dial to regulate at least one function of the dual function pump.

BRIEF DESCRIPTION OF THE DRAWINGS

FIGS. 2A-2C show images of the rete testis space that can be visualized by ultrasound and accessed by the device 100 of FIG. 1.

DETAILED DESCRIPTION

Figure 1:
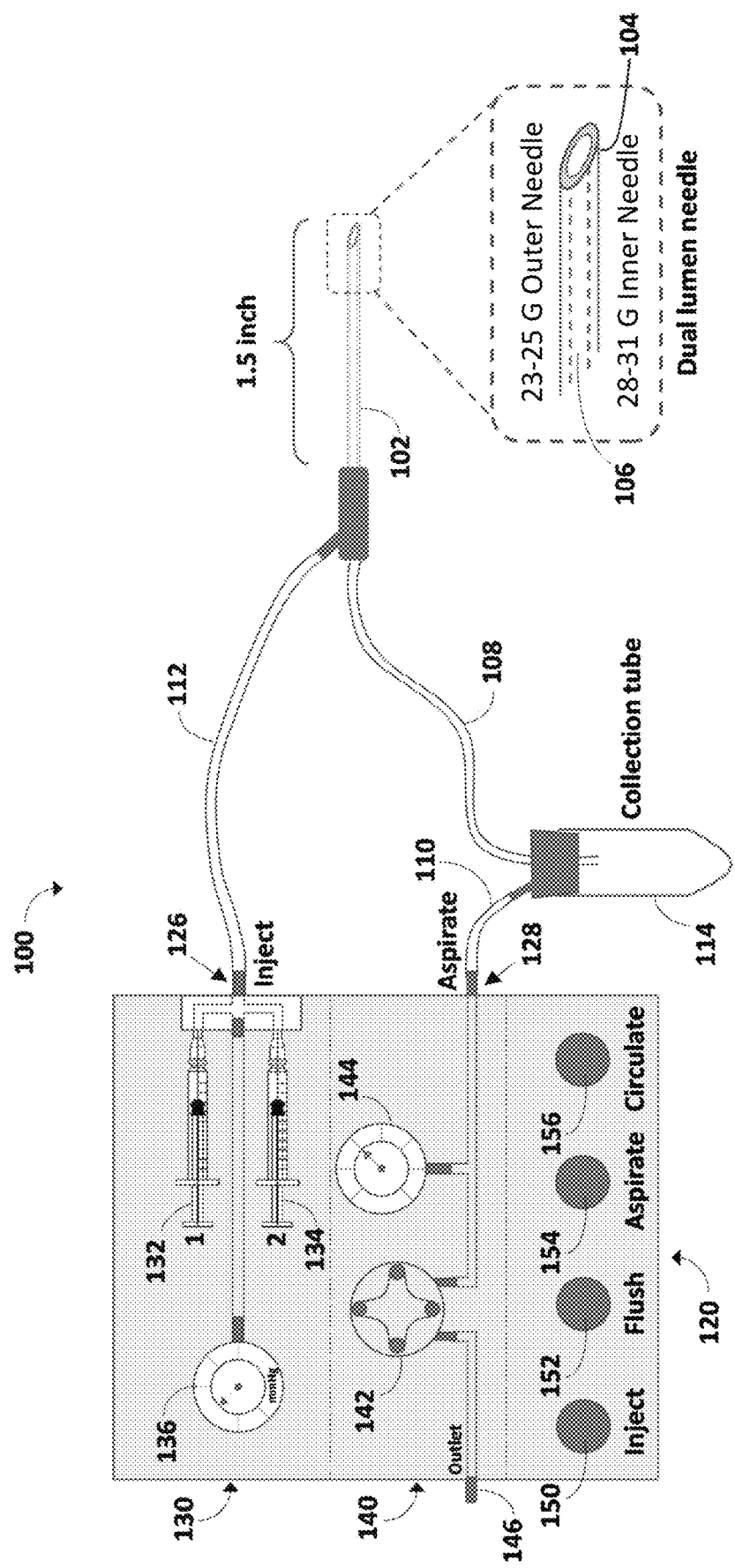
FIG. 1 shows a device 100 for delivering therapeutics to or aspirating sperm from the seminiferous tubules of the testis via the rete testis space.

For men with azoospermia, current fertility treatments typically involve invasive surgical procedures such as microsurgical testicular sperm extraction (microTESE) or less invasive treatments such as fine needle aspiration, which is less effective because it is a blind approach. Disclosed herein are apparatus and methods for a non-surgical fertility treatment for men with azoospermia and other fertility issues.

FIG. 1 shows a device 100 that can be used to non-invasively access the rete testis space for injection and/or aspiration. The device 100 includes a dual lumen needle 102, a collection line 108, an aspiration line 110, an injection line 112, a collection tube 114 and a dual function syringe/vacuum pump 120 for injection and aspiration. The dual function pump 120 includes a dual syringe pump 130 for performing injection and a vacuum pump 140 for performing aspiration. In some examples, the injection function and/or the aspiration function can be performed by one or more separate devices. In some examples, the device 100 can be used to inject a medium, stem cells, gene therapy vectors, or other therapeutics directly into the seminiferous tubules where sperm production takes place as a form of fertility treatment. In other examples, the device 100 can be used to aspirate sperm from the testis.

The dual lumen needle 102 comprises a larger gauge outer needle 104 and a smaller gauge inner needle 106, recessed within the lumen of the outer needle. Fluid can be injected through the outer needle 104 and aspirated through the inner needle 106. Injection of fluid through the outer needle 104 and aspiration of fluid through the inner needle 106 can be performed independently of each other. In the illustrated example, the outer needle 104 has a gauge in a range of 23-25 G and the inner needle 106 has a gauge in a range of 28-31 G. The outer needle 104 has the tensile strength such that it can puncture and be accurately inserted through the soft tissue of the testis. The dual lumen needle 102 has a length to reach the rete testis space. In the illustrated example, the dual lumen needle 102 has a length of about 1.5 inches. In other examples, the dual lumen needle 102 can have a length in a range of 1-2 inches.

Once the dual lumen needle 102 has been inserted to the rete testis space, a flushing medium or a flushing medium plus therapeutics can be injected through the outer needle 104. Exemplary flushing medium can include physiological saline, Hank's Balanced Salt Solution, Minimum Essential Medium Alpha, and others. The inner needle 106 can be used to aspirate media and sperm as explained in further detail below. The inner needle 106 can be recessed within the outer needle 104 to prevent suction of tissue to the tip of the inner needle.

The collection line 108 comprises a tube that connects the inner needle 106 to the collection tube 114. The aspiration line 110 comprises a tube that connects the collection tube 114 to an aspiration port 128 of the vacuum pump 140. The injection line 112 comprises a tube that connects the outer needle 104 to an injection port 126 of the dual syringe pump 130. The tubes 108, 110, 112 are flexible, which allows a user of the device 100 to have free range of motion while operating the device 100 such that the needle 102 can be accurately directed into the testis. In some examples, the tubes 108, 110, 112 are made from polyethylene.

The dual function pump 120 can both inject medium into the testis using the dual syringe pump 130 and aspirate medium with sperm from the testis using the vacuum pump 140. The pump 120 can utilize the injection port 126 for injection and flushing and the aspiration port 128 for aspiration.

The dual syringe pump 130 can comprise a first syringe 132, a second syringe 134, and a pressure sensor 136, which are all connected to the injection port 126. The first syringe 132 can contain therapeutics or flushing solution combined with therapeutics to be injected into the testis and the second syringe 134 can contain a physiological saline solution or other media fluid to flush the injection line and/or the testis. In some examples, therapeutics can include cells, viruses, recombinant nucleic acids or drugs. The first and second syringes 132, 134 can output fluids through the injection port 126. This fluid can then travel through the injection line 112 and through the outer needle 104.

The pressure sensor 136 can monitor intra-testicular pressure during operation of the device 100 to prevent overfilling of the testes, which can lead to ischemia/reperfusion injury. In some examples, the first and second syringes 132, 134 can be manually operated. In other examples, the first and second syringes 132, 134 can be automatically operated based on the operation to be performed.

The vacuum pump 140 can comprise a pump mechanism 142 and a vacuum pressure gauge 144. The pump mechanism 142 can create vacuum pressure through the aspiration port 128 to aspirate fluids through the inner needle 106, through the tube 108 and into the collection tube 114. In some examples, the pump mechanism 142 can draw air through the aspiration line 110 to create a vacuum to assist in aspiration. An outlet 146 connected to the vacuum pump 140 can allow air to exit the vacuum pump during aspiration. The vacuum pressure gauge 144 can monitor the vacuum pressure applied to the aspiration port 128 to ensure that the pressure does not exceed levels that can cause injury to a patient.

In some examples, the device 100 can be pre-flushed with a saline solution. In some examples, the device 100 can contain dials 150, 152, 154, 156 that can be used to control the flow rates through the injection line 112 and the collection line 108. In some examples, the dials 150, 152, 154, 156 can also be buttons or other actuation members that can be pressed or actuated to cause the device 100 to automatically perform certain functions as discussed in further detail below.

During operation of the device 100, ultrasound can be used to visualize the rete testis space and the dual lumen needle 102. Both the rete testis and the needle 102 appear as echodense (white) on ultrasound, as shown in FIGS. 2A-2C. The ultrasound imaging can allow the operator of the device 100 to guide the dual lumen needle 102 through the base of the scrotum into the rete testis space. Once the needle 102 has entered the rete testis space, the dual function pump 120 can either inject media into the testis, aspirate media, or aspirate media with sperm from the testis, as explained in further detail below.

In a first example, the device 100 can be used to inject stem cells or other media into the testis (e.g., germline stem cells such as spermatogonial stem cells or in vitro gem cells derived from pluripotent stem cells such as primordial germ cell-like cells). In some examples, injection can be triggered automatically by pressing or actuating button 150. The device 100 can help infuse stem cells to regenerate spermatogenesis with functional sperm in patients with infertility issues. In other examples, the device 100 can be used to inject gene therapy vectors into the testes. In operation, once the needle 102 has entered the rete testis space, the first syringe 132 can inject gene-edited stem cells, gene therapy vectors, and/or other media through the injection port 126, the injection line 112, and the outer needle 104 into the rete testis.

The second syringe 134 can be used to flush the injection port 126, the injection line 112, and the outer needle 104 to deliver the therapeutic solution (e.g., stem cells or gene therapy vectors) to the testis. In some examples, flushing can be triggered automatically by pressing or actuating button 152. During a flushing operation, the saline solution or other medium in the second syringe 134 can be injected through the injection port 126, the injection line 112, and the outer needle 104. The pressure sensor 136 can monitor intra-testicular pressure to ensure that the rete testis is not overfilled with the injection media during injection or flushing.

In another example, the device 100 can be used to aspirate sperm from the rete testis. It is often possible to retrieve sperm from the testes of men who are azoospermic using the techniques of microsurgical testicular sperm extraction (microTESE), microsurgical epididymal sperm aspiration (MESA), percutaneous epididymal sperm aspiration (PESA)

or fine needle aspiration (FNA). MicroTESE and MESA are invasive surgical procedures for retrieving sperm from the testis or epididymis, respectively. PESA and FNA are non-surgical approaches for retrieving sperm from the epididymis or testis, respectively, but they are blind approaches and the sperm recovery rates are low. Fine needle mapping to identify the region(s) of the testis with sperm is also a non-surgical, blind procedure and must be followed by another procedure (FNA or TESE) to retrieve sperm. Fine needle mapping involves many biopsies of each testis and can be traumatic.

The device 100, on the other hand, can be used to aspirate sperm directly from the rete testis space, which is contiguous with all seminiferous tubules where sperm are made. This approach is a more accurate and less traumatic procedure than those discussed above. This method is not surgical but rather involves the percutaneous insertion of the needle 102 into the rete testis space. Because the device can be operated with the guidance of ultrasound, it can be accurately inserted into the rete testis that is contiguous with all seminiferous tubules where sperm are made. Therefore, once inserted into the rete testis space, the device 100 can simultaneously flush and/or aspirate from all seminiferous tubules of the testis at the same time.

In operation, once the needle 102 has accessed the rete testis space, the first syringe 132 or the second syringe 134 can inject saline or other media through the injection line 112 to flush the seminiferous tubules via the rete testis. In some examples, this flushing operation can be performed automatically by pressing or actuating button 150 or 152 as explained above. After performing this flushing operation, the solution can flush sperm and/or testicular exudates from the seminiferous tubules, which can then be aspirated via the inner needle 106. This causes sperm to be flushed directly from all seminiferous tubes simultaneously. The sperm can be aspirated through the inner needle 106 and the collection line 108 and can be collected in the collection tube 114. The collected sperm can be used later for fertility treatments. This method of retrieving sperm from the testis is less invasive, less time consuming, and may have a higher success rate than other sperm retrieval methods discussed above. In some examples, aspiration can be triggered automatically by pressing or actuating button 154.

In some examples, injection through the injection port 126 and aspiration through the aspiration port 128 can occur simultaneously or in an alternating fashion to circulate solution through the testis and into the collection tube 114. In some examples, circulation can be triggered automatically by pressing or actuating button 156.

The disclosed methods, apparatus, and systems should not be construed as limiting in any way. Instead, the present disclosure is directed toward all novel and nonobvious features and aspects of the various disclosed embodiments, alone and in various combinations and sub combinations with one another. The disclosed methods, apparatus, and systems are not limited to any specific aspect or feature of combination thereof, nor do the disclosed embodiments require that any one or more specific advantages be present or problems be solved. Any of the herein described features can be combined with any other features in different embodiments of the technology without limitation, unless physically impossible, and all such combinations are considered to be within the scope of the disclosure and part of the inventions disclosed herein.

In view of the many possible embodiments to which the principles of the disclosed technology may be applied, it should be recognized that the illustrated embodiments are only preferred examples of the technology and should not be taken as limiting the scope of the disclosure. Rather, the scope of the disclosure is at least as broad as the following claims. We therefore claim all that comes within the scope of these claims and their equivalents.

The invention claimed is:

1. An apparatus comprising:
   a dual lumen needle comprising an outer needle having a first gauge and an inner needle having a second gauge, wherein the first gauge is larger than the second gauge, and wherein the inner needle is recessed within a lumen of the outer needle;
   a collection tube;
   a dual function pump comprising:
      a dual syringe pump comprising a first syringe, a second syringe, a pressure sensor, and an injection port, wherein the first syringe and the second syringe are configured to output fluid media through the injection port; and
      a vacuum pump comprising a vacuum pressure gauge and an aspiration port;
   a first flexible tube connecting the injection port to the outer needle of the dual lumen needle;
   a second flexible tube connecting the aspiration port to the collection tube; and
   a third flexible tube connecting the inner needle of the dual lumen needle to the collection tube.

2. The apparatus of claim 1, wherein the first, second, and third flexible tubes comprise polyethylene.

3. The apparatus of claim 1, wherein the inner needle is configured to aspirate fluid into the collection tube.

4. The apparatus of claim 1, wherein the outer needle is configured to inject fluid from the first syringe or the second syringe.

5. The apparatus of claim 1, wherein the dual function pump is configured to inject a first fluid or fluids through the injection port into a testis and then to aspirate the first fluid or fluids with testicular exudates through the inner needle of the dual lumen needle.

6. The apparatus of claim 1, wherein the pressure sensor is configured to monitor intra-testicular pressure of a patient when the dual lumen needle is inserted into a rete testis space of the patient.

7. The apparatus of claim 1, wherein the vacuum pump is configured to apply vacuum pressure to the aspiration port to cause fluid to be aspirated through the inner needle.

8. The apparatus of claim 1, wherein the vacuum pressure gauge is configured to monitor vacuum pressure applied to the aspiration port.

9. The apparatus of claim 1, wherein the outer needle has a gauge in a range of 23-25 G.

10. The apparatus of claim 1, wherein the inner needle has a gauge in a range of 28-31 G.

11. The apparatus of claim 1, further comprising at least one dial to regulate at least one function of the dual function pump.

12. The apparatus of claim 1, wherein the apparatus is configured to inject therapeutic medium comprising stem cells into a rete testis space and seminiferous tubules of a testis.

13. A method, comprising:
   inserting the dual lumen needle of the apparatus of claim 9 into a rete testis space of a testis of a patient; and
   injecting a therapeutic medium through the dual lumen needle into the rete testis space and seminiferous tubules of the testis, wherein the therapeutic medium helps to treat infertility.

14. The method of claim 13, further comprising monitoring intra-testicular pressure of the patient.

15. The method of claim 13, wherein the therapeutic medium comprises stem cells.

16. The method of claim 13, wherein the therapeutic medium comprises gene therapy vectors.

17. The method of claim 13, further comprising flushing the rete testis space with a saline solution through the dual lumen needle.

18. A method, comprising:
   inserting the dual lumen needle of the apparatus of claim 9 into a rete testis space of a patient;
   flushing the rete testis space with a saline solution through the outer needle of the dual lumen needle; and
   aspirating sperm from the rete testis space through the inner needle of the dual lumen needle.

19. The method of claim 18, further comprising monitoring intra-testicular pressure of the patient.

20. The method of claim 18, further comprising collecting the aspirated sperm in the collection tube.

* * * * *